United States Patent [19]

Recsei

[11] Patent Number: 4,931,390
[45] Date of Patent: Jun. 5, 1990

[54] EXPRESSION OF THE CLONED LYSOSTAPHIN GENE

[75] Inventor: Paul A. Recsei, New York, N.Y.

[73] Assignee: Public Health Research Institute of the City of New York, Inc., New York, N.Y.

[21] Appl. No.: 34,464

[22] Filed: Apr. 10, 1987

Related U.S. Application Data

[63] Continuation-in-part of Ser. No. 852,407, Apr. 16, 1986, abandoned.

[51] Int. Cl.$^5$ .................. C12N 9/00; C12N 21/02; C12N 21/00; C12N 15/00; C12N 1/00; C12N 1/20; C12N 1/16; C12N 1/18; C07H 21/04
[52] U.S. Cl. .................................. 435/183; 435/69.1; 435/220; 435/172.3; 435/243; 435/252.3; 435/252.31; 435/252.33; 435/252.35; 435/255; 435/256; 435/320; 536/27; 935/11; 935/29; 935/69; 935/72; 935/73; 935/74; 935/75
[58] Field of Search .................. 435/68, 70, 71, 91, 435/172.1, 172.3, 320, 183, 252.3, 252.31, 252.35, 243, 255, 256, 220; 536/27; 935/9, 11, 14, 29, 72–75

[56] References Cited

U.S. PATENT DOCUMENTS 3,278,378 10/1966 Schindler et al. ............... 435/68
4,467,036 8/1984 Schnepf et al. ................. 435/68
4,617,266 10/1986 Fahnestock .................... 435/68

OTHER PUBLICATIONS

Trayer et al; J. Biol. Chem. 245: 4842 (1970).
Schindler et al; Proc. Natl. Acad. Sci. U.S.A. 51: 414 (1964).
Sloan et al; Int. J. Systematic Biol. 32: 170 (1982).
Gryczan et al; J. Bacteriol. 141: 246 (1980).
Polak et al; Plasmid 7: 152 (1982).
Vieira et al; Gene 19: 259 (1982).
Yanisch-Perron et al; Gene 33: 103 (1985).
American Type Culture Collection Catalogue of Strains I, 15th Edition, 1982, p. 80.
Paul A. Recsei, "Cloning, Sequence, and Expression of the Lysostaphin Gene from Staphylococcus Simulans"; Proc. Natl. Acad. Sci. U.S.A., vol. 84, pp. 1127–1131, Mar. 1987 Biochemistry.
L. S. Heath et al., "Expression in *Escherichia coli* of the Gene Encoding Lysostaphin Endopeptidase," (Abstr.) 87th Annual Meeting of the American Society for Microbiology, 1987.

Primary Examiner—James Martinell
Attorney, Agent, or Firm—White & Case

[57] ABSTRACT

The present invention provides recombinant plasmids which is transformant microbial hosts express lysostaphin, a bacteriocin that kills most known staphylococcal species. The invention also provides lysostaphin, substantially free from non-lysostaphin contaminants. Recombinant plasmids, pRG5, pJP1, pDF8 and pRP1, were derived by inserting a 1.5 kilobase segment of DNA coding for lysostaphin into the cloning vectors, pUC8, pBC16, pBD64 and pSPV1, respectively. *E. coli* strain JM105 transformed by pRG5 and members of *Bacillus* species, including *B. subtilis* and *B. sphaericus* transformed by pJP1, pDF8 and pRP1 produce lysostaphin which is immunologically and electrophoretically indistinguishable from that produced by *S. simulans*, the natural source. Furthermore, *B. sphaericus* strain 00/pJP1 transformants produce five times the amount of lysostaphin as *S. simulans*. The invention also provides the 1.5 kbp DNA fragment coding for lysostaphin. The sequence of the DNA encodes preprolysostaphin, a monomeric 389 amino acid protein, which is posttranslationally processed to mature lysostaphin.

23 Claims, 1 Drawing Sheet

EXPRESSION OF THE CLONED LYSOSTAPHIN GENE

BACKGROUND OF THE INVENTION

The application is a countinuation-in-part of U.S. application Ser. No. 852,407, filed Apr. 16, 1986, now abandoned. The present invention relates to novel plasmids which in transformant microbial hosts express the gene for lysostaphin. The invention also relates to lysostaphin so produced.

Lysostaphin is a bacteriocin secreted by a single known strain of Staphylococcus simulans orgininally isolated and named Staphylococcus staphylolyticus by Schindler and Schuhardt. The production of lysostaphin by S. staphylolyticus has been described previously in U.S. Pat. No. 3,278,378 issued Oct. 11, 1966 and in Proceedings of the National Academy of Sciences, Vol. 51, pp. 414–421 (1964). The single organism S. staphylolyticus (NRRL B-2628) which produces lysostaphin was recently identified as a biovar of S. simulans by Sloan et al., Int. J. System. Bacteriol., Vol. 32, pp. 170–174 (1982). Since the name S. staphylolyticus is not on the Approved List of Bacterial Names, the organism producing lysostaphin has been redesignated as S. simulans.

Bacteriocins are proteins secreted by bacteria that kill and sometimes lyse related bacteria. For example, lysostaphin lyses and kills practically all known staphylococcal species but is inactive against bacteria of all other genera. Although its catalytic properties are not well characterized, lysostaphin has been shown to be endopeptidase which apparently cleaves the polyglycine cross-links of the peptidoglycan found in the cell walls of staphylococci.

Lysostaphin production occurs during the stationary phase of S. simulans cultures grown under certain conditions and appears to be coordinated with production of other extracellular enzymes. Cultures that produce lysostaphin appear to be resistant to its activities while cultures grown under non-producing conditions are sensitive.

Previous studies have shown that lysostaphin can be producted by fermentation techniques wherein S. simulans is grown in liquid culture. Such fermentation techniques are described in U.S. Pat. No. 3,278,378 issued Oct. 11, 1966 and in Proceedings of the National Academy of Sciences, Vol. 51, pp. 414–421 (1964). Various improvements in the production of lysostaphin by fermentation techniques have also been made as documented in U.S. Pat. Nos. 3,398,056 issued Aug. 20, 1968; and 3,594,284 issued Jul. 20, 1971. The latter two references disclose improvements in culture medium and inoculation techniques whereby the production of lysostaphin by fermentation can be accelerated and improved. Production and purification of lysostaphin by known techniques, however, results in a product that is contaminated to some degree by other staphylococcal products. Immunization of animals or man with lysostaphin contaminated by non-lysostaphin immunogenic material from staphylococci might result in an undesirable, and potentially adverse, immunological response.

Lysostaphin isolated from culture filtrates of S. simulans has been characterized as a zinc-containing protein composed of a single polypeptide chain with a molecular weight of about 25,000 daltons. It is heat labile, nondialyzable and has an isoelectric point of about pH 11. Futhermore, the capacity of lysostaphin to lyse viable and heat-killed staphylococci and staphylococcal cell walls is destroyed by treatment with the enzyme trypsin.

Recombinant DNA techniques, whereby genes for a variety of proteins can be cloned by insertion into a plasmid, cosmid, or phage vector which can then be used to transform a microorganism, have been used widely to study the structure and expressions of genes and to produce a ready source of various pure proteins for various purposes. There have been, however, no reports relating to such cloning techniques being used to insert the gene encoding lysostaphin into a cloning vector to construct novel vectors which can transform a microorganism, other than S. simulans (NRRL B-2628), to allow the production of large amounts of lysostaphin.

BRIEF SUMMARY OF THE INVENTION

In accordance with the present invention, recombinant plasmids are described which in transformant microbial hosts will express a gene encoding lysostaphin. The recombiant plasmids were derived by inserting an identified DNA sequence which codes for lysostaphin into suitable cloning vectors.

Suitable cloning vectore include those which replicate in bacteria, including, inter alia, E. coli, Bacillus spp., and Streptomyces, and yeast. Host microorganisms include E. coli, Bacillus spp., Streptomyces, and yeast. The invention, however, is not limited to the above vectors and microbial hosts. It will be apparent to those skilled in the art that other vectors and hosts can be used in the practice of the invention.

In one embodiment, the DNA sequence coding for lysostaphin was inserted into the E. coli plasmid pUC8, a well-known cloning vector, to create recombinant plasmid pRG5. E. coli JM105 transformed by pRG5 produces lysostaphin.

In another embodiment of this invention, the lysostaphin gene from pRG5 was cloned into Bacillus plasmids pBC16, pBD64 and pSPV1 whereby recombinant plasmids, pJP1, pDF8 and pRP1, respectively were produced. Members of Bacillus species, including B. subtilis, transformed by one or another of these three recombinant Bacillus plasmids containing the gene for lysostaphin, secreted large amounts of lysostaphin into the culture medium. The invention further provides for B. sphaericus strain 00 which, when transformed by recombinant plasmid pJPI, produces about five times the amount of lysostaphin as can be obtained from cultures of S. simulans, (NRRL B-2628), the natural producer.

The lysostaphin expressed as a result of transformation of microbial hosts by the above-mentioned plasmids and other plasmids containing the lysostaphin gene is substantially free of non-lysostaphin contaminants, especially immunogenic staphylococcal contaminants.

The invention further provides a 1.5-kilobase pair (kbp) DNA fragment encoding lysostaphin, the sequence of such gene, and the 389 amino acid protein, preprolysostaphin, having a molecular weight of about 42,200 daltons which is encoded by the DNA fragment. The amino terminal sequence of preprolysostaphin contains a cluster of four positively charged amino acid residues followed by an uncharged largely hydrophobic sequence and, therefore, has the properties of a signal peptide. Adjacent to the lysostaphin signal peptide is the prolysostaphin amino acid sequence. The "pro"

sequence contains seven tandem repeats of a homologous 13 amino acid sequence which are removed during processing to mature enzyme.

The 1.5 kbp DNA fragment which contains the lysostaphin structural gene, therefore, codes for a preproenzyme protein (preprolysostaphin), which is subsequently processed to mature active lysostaphin having a molecular weight of approximately 26,920 daltons. It was heretofor unknown that lysostaphin was synthesized in presursor form which is subsequently processed to an active enzyme.

Also encompassed within the scope of this invention are DNA fragments which are homologous to the 1.5 kbp DNA fragment which codes for lysostaphin provided in Formula I and which code for functionally equivalent proteins.

The invention also provides for preprolysostaphin, prolysostaphin and lysostaphin, which is substantially free of non-lysostaphin immunogenic staphylococcal contaminants. The invention further encompasses those portions of the 1.5 kbp DNA fragment which code for the lysostaphin signal peptide, the prolysostaphin sequences, and the mature active lysostaphin, respectively. DNA fragments which are homologous to these three portions of the 1.5 kbp DNA fragment encoding lysostaphin and which encode functionally equivalent peptides are also within the scope of the invention.

BRIEF DESCRIPTION OF THE DRAWING

The present invention is now described with reference to the following detailed description, Examples and figures in which.

DESCRIPTION OF THE PREFERRED EMBODIMENTS

Figure 1:
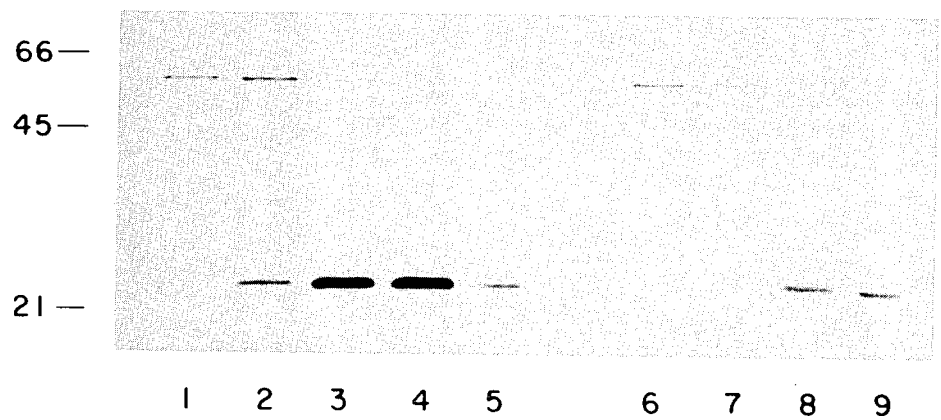
FIG. 1 is an immunoblotted electropherogram showing the production of lysostaphin and prolysostaphin by *E. coli*/pRG5 transformants and *S. simulans*.

The present invention provides for recombinant plasmids which have been created by inserting the 1.5 DNA fragment which codes for lysostaphin into cloning vectors that replicate in various host microorganisms. Particularly preferred host organisms are *E. coli* and strains of *Bacillus subtilis, Bacillus sphaericus* and other *Bacillus* species. The 1.5 kbp DNA fragment is stably maintained and lysostaphin is expressed at high levels in cloned transformant bacteria harboring the plasmids. The 1.5 kbp DNA fragment coding for lysostaphin was isolated from *S. simulans* (NRRL B-2628) and is present in this organism on a large penicillinase plasmid. A proenzyme with a molecular weight of about 42,200 daltons has now been shown to be produced by *S. simulans*. When the 1.5 kbp DNA fragment coding for lysostaphin is inserted into the plasmids of the present invention, lysostaphin expressed by the transformant microorganisms is secreted from the cells. Mature lysostaphin accumulates in large quantities in the medium in which the transformants are growing. Some of the genetically engineered transformant *Bacillus* strains produce considerably more lysostaphin per ml of culture supernatant than does *S. simulans*, the natural source of the enzyme.

The present invention, in particular, provides for plasmid, pRG5, which was derived from the *E. coli* cloning vector pUC8 by inserting the 1.5 kbp DNA fragment coding for lysostaphin into the lacZ' gene of plasmid pUC8. Latelogarithmic phase cultures of *E. coli* strain JM105, which is the host bacteria for recombinant plasmids derived from pUC8, transformed by pRG5 had detectable levels of lysostaphin activity in the supernatant, periplasmic, and cytoplasmic fractions.

Furthermore, the present invention also particularly provides for recombinant plasmids into which the 1.5 kbp DNA fragment coding for lysostaphin has been inserted that can be used to transform *Bacillus* species. The invention thus provides for recombinant *Bacillus* plasmids pJP1, pDF8, and pRP1 which in a transformant host express lysostaphin. The plasmids were constructed by inserting the 1.5 kbp DNA fragment which codes for lysostaphin that is obtained from pRG5 into *Bacillus* plasmids pBC16, pBD64 and pSPV1 respectively. A further embodiment of this invention includes the transformant *Bacillus* species that produce and secrete lysostaphin upon transformation with these plasmids. Plasmids pJP1, pDF8, and pRP1 have been used to transform *B. subtillis* and *B. sphaericus*. The particularly preferred recombinant plasmid of this invention for use in *Bacillus* species is pJP1. The particularly preferred transformant host organisms expressing lysostaphin are competent *Bacillus subtilis* BD170 and *Bacillus sphaericus* 00 strains.

In particular, *B. sphaericus* strain 00 transformed by pJP1 produced at least five times the amount of lysostaphin per liter of culture as *S. simulans*, (NRRL B-2628). The recombinant product isolated from *B. sphaericus* strain 00/pJP1 is indistinguishable from the *S. simulans* lysostaphin on the basis of electrophoretic mobility, immunologic cross-reactivity with lysostaphin-specific antibodies, catalytic activity. Lysostaphin produced by transformant microorganisms according to this invention is substantially free of non-lysostaphin contaminants, in particular immunogenic staphylococcal contaminants.

The invention also provides for the cloned 1.5 kbp DNA fragment coding for lysostaphin, the sequence of which is provided in Formula I. The DNA sequence is characterized by an open reading frame extending from a TTG initiation codon at nucleotides 245-247 to a TGA termination codon at nucleotides 1412-1414 which encodes the 389 amino acid preprolysostaphin. It will be understood that DNA fragments homologous in sequence to the sequence in Formula I and which code for functionally equivalent proteins are within the scope of the invention.

*E. coli* JM105 carrying pRG5, ATCC Accession No. 67076; *B. subtilis* BD170 carrying pJP1, ATCC Accession No. 67078; *B. sphaericus* 00 carrying pJP1, ATCC Accession No. 67080; *B. subtilis* BD 170 carrying pDF8, ATCC Accession No. 67077; and *B. subtilis* BD 170 carrying pRP1, ATCC Accession No. 67079 are on deposit with the American Type Culture Collection, 12301 Parklawn Drive, Rockville, Md. USA.

The following examples are provided to illustrate the invention and are not intended to limit the same.

EXAMPLE 1

Construction of pRG5

Plasmid pRG5 was contructed by inserting the 1.5 kbp DNA fragment which codes for lysostaphin into the lacZ' gene of plasmid pUC8, an engineered cloning vector described by Vieira and Messing, Gene, Vol. 19, pp. 259–268 (1982).

Total DNA was isolated from *S. simulans* (NRRL B-2628) as follows:

*S. simulans* was grown to midlogarithmic phase in Casamino Acids medium described by Robinson et al. J. Bacteriol. Vol. 137, pp. 1158–1164 (1979). The cells were harvested by centrifugation, washed in Tris buffer (50 mM Tris, 50 mM EDTA, pH 7.8), and resuspended to 20% of the original culture volume in Tris buffer containing 50 µg/ml lysostaphin (obtained from Mead-Johnson) and lysozyme (0.5 mg/ml). After a 2 hour incubation at 37° C., pronase (1 mg/ml) and sodium dodecysulfate (0.6%) were added and the suspension incubated a further 2 hours at 37° C. The *S. simulans* lysate thus obtained by this treatment was extracted two times with an equal volume of phenol using standard techniques.

Nucleic acid was precipitated from the aqueous phase of the phenol-extractred lysate by the addition of two volumes of ice-cold 95% ethanol, collected by centrifugation, and dissolved in TE buffer (10 mM Tris, 1 mM EDTA, pH 8.0). The dissolved nucleic acid was digested for 2 hours at 37° C. with a combination of pancreatic ribonuclease (30 µg/ml) and T1 ribonuclease (2 U/ml) to degrade any RNA present in the sample. The resulting DNA was again precipitated wtih ethanol and dissolved in TE buffer. Approximately 1.5 mg of *S. simulans* DNA was isolated from a 0.5 L culture of mid log phase cells.

Cloning was carried out using pUC8 as the vector and *E. coli* K12 strain JM105 as the host. Total *S. simulans* DNA, isolated as described above, was partially digested with Mbo I and fractionated by centrifugation through a 12 ml 10–30% sucrose gradient at 35,000 rpm for 20 hours. Ten µg of DNA fragments ranging in size from 5–15 kilobase pairs (kbp), with a 10 kbp average size, were pooled and ligated to two µg of Bam HI-digested pUC8. This plasmid confers ampicillin resistance and carries the lacZ' gene which codes for the amino terminal portion of *E. coli* beta-galactosidase. Insertion of foreign DNA into the cloning site located in the lacZ' gene results in inactivation of beta-galactosidase.

Approximately 80% of the JM105 transformants obtained from this procedure contained recombinant plasmids as indicated by the inactivation of the lacZ' gene (lacZ'−), i.e., the transformants did not produce beta-galactosidase.

To screen for lysostaphin expression in the transformants, *S. aureus* RN492, described by Novick et al., Plasmid, Vol. 2, pp. 109–129 (1979) and obtained therefrom, was used as the indicator strain. This bacterial strain is a constitutive beta-lactamase producer and is relatively resistant to ampicillin. *E. coli* JM105 transformants grown on L agar containing 50 µg/ml ampicillin were exposed to chloroform vapor for 30 minutes to lyse them and overlaid with a 0.1% (v/v) suspension of a stationary phase culture of *S. aureus* RN492 in GL agar. Production of lysostaphin by *E. coli* JM105 transformants, indicating the successful insertion of the lysostaphin gene into pUC8, was determined by observation of lysis of the indicator cells superimposed on a JM105 transformant colony. Approximately nine out of 1000 clones harboring recombinant plasmids (amp+, lacZ'−) contained the lysostaphin gene, a number which suggested that multiple copies of the lysostaphin gene were present per chromosomal equivalent of *S. simulans* DNA (about 2000 kbp).

Lysostaphin-producing transformants contained recombinant plasmids having inserts of 6.0, 6.5, or 8.0 kbp. Restriction analysis showed that these inserts were present in either orientation in the cloning vector and contained a 4.3 kbp DNA fragment in common. The DNA sequence coding for lysostaphin was further localized to a 1.5 kbp Hpa II-Hind III DNA fragment obtained from the 4.3 kbp DNA fragment. This 1.5 kbp DNA fragment was recloned into the Acc I-Hind III sites of pUC8 to create the recombinant plasmid pRG5, which is a preferred embodiment of this invention.

EXAMPLE 2

Sequence and Characteristic of the 1.5 kbp DNA Fragment Coding for Lysostaphin

The DNA sequence of the pRG5 1.5 kbp DNA fragment coding for lysostaphin was determined by the dideoxy chain termination method of Sanger et al., Proc. Natl. Acad. Sci., Vol. 74, pp. 5463–5467 (1977) using the phage vectors M13mp10 and M13mp11 as described by Messing, Meth. Enzymol., Vol. 101, pp. 20–78 (1983).

The nucleotide sequence of the entire 1.5 kbp DNA fragment coding for lysostaphin, is provided as Formula I. With reference to Formula I, the 1.5 kbp DNA fragment contains an open reading frame of 1,167 nucleotides which extends from a TTG initiation codon at nucleotides 245–247 to a TGA termination codon at nucleotides 1412–1414. The DNA fragmént also contains a presumed promotor with −35 and −10 regions at nucleotides 89–95 and 110–119, which are underlined in Formula I. The lysostaphin promotor appears homologous to *B. subtilis* promotors recognized by the σ37 regulatory subunit of RNA polymerase described by Wong et al., Proc. Natl. Acad. Sci., Vol. 81, pp. 1184–1188 (1984). A ribosome-binding sequence, AGGAGGT, at nucleotides 231–237, with complete complimentary to the mRNA binding sequence of 16S ribosomal RNA, can also be found in the DNA sequence seven base pairs before the TTG initiation codon coding for f-Met.

The open reading frame encodes preprolysostaphin, a 389 amino acid protein having a molecular weight of approximately 42,200 daltons, which is the precursor to mature enzymatically active lysostaphin. The amino acid sequence for preprolysostaphin, deduced from the DNA sequence, is also given in Formula I. It was heretofor unknown that lysostaphin was synthesized in a precursor form.

FORMULA I

1: ccggaactcttgaatgtttagttttgaaaattccaaaaaaaaacctactttcttaatatt

61: gattcatatattttaacacaatcagttagaatttcaaaaatcttaaagtcaatttttga

121: gtgtgtttgtatatttcatcaaaatcaatcaatattatttactttcttcatcgttaaaa

181: aatgtaatatttataaaaatatgctattctcataaatgtaataataaattaggaggtatt

241: aaggttgaagaaaacaaaaaacaattattatacgagaccttagctattggactgagtac f-MethLysLysThrLysAsnAsnTyrTyrThrArgProLeuAlaIleGlyLeuSerThr 301: atttgccttagcatctattgtttatggagggattcaaaatgaaacacatgcttctgaaaa PheAlaLeuAlaSerIleValTyrGlyGlyIleGlnAsnGluThrHisAlaSerGlulys 361: aagtaatatggatgtttcaaaaaaagtagctgaagtagagacttcaaaagccccagtaga SerAsnMetAspValSerLysLysValAlcGluValGluThrSerLysAlaProValGlu 421: aaatacagctgaagtagagacttcaaaagctccagtagaaaatacagctgaagtagagac AsnThrAlaGluVal- GluThrSerLysAlaProValGluAsnThrAlaGluVal-
GluThr 481: ttcaaaagctccagtagaaaatacagctgaagtagagactt-
caaaagctccagtagaaaa SerLysAlaProValGluAsn-
ThrAlaGluValGluThrSerLysAlaProValGluAsn 541: tacagctgaagtagagacttcaaaagctccggtagaaaatacagct-
gaagtagagacttc ThrAlaGluValGluThrSerLysAla-
ProValGluAnsThrAlaGluValGluThrSer 601: aaaagccccagtagaaaatacagctgaagtagagactt-
caaaagcccctggttcaaaatag LysAlaProValGluAsn-
ThrAlaGluValGluThrSerLysAlaLeuValGlnAs-
nArg 661: aacagctttaagagctgcaacacatgaacattcagcacaatggtt-
gaataattacaaaaa ThrAlaLeuArgAlaAlaThrHis-
GluHisSerAlaGlnTrpLeuAsnAsnTyrLysLys 721: aggatatggttacggtccttatccattaggtataaatggcggtatg-
cactacggagttga GlyTyrGlyTyrGlyProTyrProLeu-
GlyIleAsnGlyGlyMetHisTyrGlyValAsp 781: ttttttatgaatattggaacaccagtaaaagctatttcaagc-
ggaaaaatagttgaagc PhePheMetAsnIleGlyThr-
ProValLysAlaIleSerSerGlyLysIleValGluAla 841: tggttggagtaattacggaggaggtaatcaaataggtcttatt-
gaaaatgatggagtgca GlyTrpSerAsnTyrGlyGly-
GlyAsnGlnIleGlyLeuIleGluAsnAspGlyValHis 901: tagacaatggtatatgcatctaagtaaatataatgttaaagtag-
gagattatgtcaaagc ArgGlnTrpTyrMetHisLeuSerLys-
TryAsnValLysValGlyAspTryValLysAla 961: tggtcaaataatcggttggtctggaagcactggttattctacagcac-
cacatttacactt GlyGlnIleIleGlyTrpSerGlySerThr-
GlyTrySerThrAlaProHisLeuHisPhe 1021: ccaaagaatggttaattcattttcaaattcaactgcccaagatc-
caatgcctttcttaaa GlnArgMetValAsnSerPheSerAsn-
SerThrAlaGlnAspProMetProOheLeuLys 1081: gagcgcaggatatggaaaagcaggtggtacagtaact-
ccaacgccgaatacaggttggaa SerAlaGlyTyrGlyLysAla-
GlyGlyThrValThrProThrProAsnThrGlyTrpLys 1141: aacaaacaaatatggcacactatataaatcagagtcagctagctt-
cacacctaatacaga ThrAsnLysTyrGlyThrLeuTyrLys-
SerGluSerAlaSerOheThrProAsnThrAsp 1201: tataataacaagaacgactggtccatttagaagcatgccgcagt-
caggagtcttaaaagc IleIleThrArgThrThrGlyProP-
heArgSerMetProGlnSerGlyValLeuLysAla 1261: aggtcaaacaattcattatgatgaagtgatgaaacaagacggt-
catgtttgggtaggtta GlyGlnThrIleHisTyrAspGluVal-
MetLysGlnAspGlyHisValTrpValGlyTyr 1321: tacaggtaacagtggccaacgtatttacttgcctgtaagaacatg-
gaataaatctactaa ThrGlyAsnSerGlyGlnArgIleTyr-
LeuProValArgThrTrpAsnLysSerThrAsn 1381: tactttaggtgtctttggggaactataaaagtgagcgcgctttt-
tataaacttatatgat ThrLeuGlyValLeuTrpGlyThrIle-
Lys 1441: aattagagcaaataaaaattttttctcattcctaaagttgaagc The amino therminal 36 amino acid sequence of pro-
prolysostaphin is the signal peptide, i.e. the largely hy-
drophobic region found in precursors of secreted prote-
ins.

Signal peptides are the amino terminal sequences of
secreted proteins as translated which are involved in
directing the growing polyeptide chain through the
membrane after synthesis on membrane-bound ribo-
somes. In eukaryotes, the signal peptide is cleaved off
by a specific protease found in the lumenal side of the
rough endoplasmic reticulum (RER), even before poly-
peptide synthesis is completed.

In bacteria, which do not have an RER, secreted
proteins are synthesized on ribosomes which may be
bound to the internal face of the plasma membrane. The
signal peptide of nascent bacterial polypeptide chains
appears to be involved in transporting the protein
through the plasma membrane. Bacterial signal pep-
tides, in general, are removed during or shortly after
transport through the plasma membrane, since secreted
proteins that accumulate in culture medium no longer
contain this sequence.

Several features of preprolysostaphin can be seen
with reference to Formula II which depicts the amino
terminal 152 amino acids of preprolyspstaphin (A) and
the nucleotide sequence of the 1.5 kbp DNA fragment
from base pairs 389-661 (B).

The signal peptide or signal sequence of secreted or
membrane bound proteins is characterized by a high
content of hydrophobic amino acids as is apparent in the
signal peptide of preprolysostaphin shown in Formula
IIA. Although the hydrophobicity of any signal se-
quence is a constant finding, the actual amino acids
contained therein, the particular sequence of the amino
acids and the length of the peptide can vary widely. For
example, usually long signal sequences (31-44 amino
acids) occur in *Bacillus* species. Watson, Nucleic Acids
Res., Vol. 12, pp. 5145-5164, 1984.

The cleavage site of the preprolysostaphin signal
sequence is the Ala-Ser bond at amino acid residues
36-37 (Formula IIA). Removal from the 1.5 kbp DNA
fragment of the DNA coding for the signal sequence of
preprolysostaphin would most likely result in a non-
secreted protein. A DNA sequence coding for a func-
tionally equivalent signal peptide which replaces the
DNA encoding the lysostaphin signal peptide would
also most likely encode a secreteable "preprolysosta-
phin;" albeit one with a different, but functional signal
peptide.

Following cleavage of the signal sequence which is
required for secretion, the protein that accummulates
and is subsequently processed is prolysostaphin. Also
shown in Formula IIA is the sequence from Ala-49
through ARG-139 of prolysostaphin which contains
seven tandem repeats of a 13 amino acid sequence. This
portion of the protein, which contains a large amount of
glutamic acid and has a net negative charge, is cleaved
off during the processing of prolysostaphin to mature
lysostaphin. The DNA sequence, i.e. bp 389 to 661,
which codes for the amino acid repeats is composed of
seven repeats of an homologous 39 bp sequence. (For-
mula IIB). The seven tandem amino acid repreats (IIA)
and corresponding nucleotide sequence repeats (IIB)
are numbered 1-7 in Formula II.

FORMULA II

A

| | | | | f-MET$_1$ | LYS | LYS | THR | LYS | ASN | ASN | TYR | TYR |
|---|---|---|---|---|---|---|---|---|---|---|---|---|
| | THR | ARG | PRO | LEU | ALA | ILE | GLY | LEU | SER | THR | PHE | ALA | LEU |
| | ALA | SER | ILE | VAL | TYR | GLY | GLY | ILE | GLN | ASN | GLU | THR | HIS |
| | ALA$_{36}$ | SER$_{37}$ | GLU | LYS | SER | ASN | MET | ASP | VAL | SER | LYS | LYS | VAL |
| 1 | ALA$_{49}$ | GLU | VAL | GLU | THR | SER | LYS | ALA | PRO | VAL | GLU | ASN | THR |
| 2 | ALA | GLU | VAL | GLU | THR | SER | LYS | ALA | PRO | VAL | GLU | ASN | THR |
| 3 | ALA | GLU | VAL | GLU | THR | SER | LYS | ALA | PRO | VAL | GLU | ASN | THR |
| 4 | ALA | GLU | VAL | GLU | THR | SER | LYS | ALA | PRO | VAL | GLU | ASN | THR |
| 5 | ALA | GLU | VAL | GLU | THR | SER | LYS | ALA | PRO | VAL | GLU | ASN | THR |
| 6 | ALA | GLU | VAL | GLU | THR | SER | LYS | ALA | PRO | VAL | GLU | ASN | THR |
| 7 | ALA | GLU | VAL | GLU | THR | SER | LYS | ALA | LEU | VAL | GLN | ASN | ARG$_{139}$ |
| | THR | ALA | LEU | ARG$_{143}$ | ALA$_{144}$ | ALA | THR | HIS | GLU | HIS | SER | ALA | GLN |

B

| | | | | | | | | | | | | |
|---|---|---|---|---|---|---|---|---|---|---|---|---|
| 1 | GCT | GAA | GTA | GAG | ACT | TCA | AAA | GCC | CCA | GTA | GAA | AAT | ACA |
| 2 | GCT | GAA | GTA | GAG | ACT | TCA | AAA | GCT | CCA | GTA | GAA | AAT | ACA |
| 3 | GCT | GAA | GTA | GAG | ACT | TCA | AAA | GCT | CCA | GTA | GAA | AAT | ACA |
| 4 | GCT | GAA | GTA | GAG | ACT | TCA | AAA | GCT | CCA | GTA | GAA | AAT | ACA |
| 5 | GCT | GAA | GTA | GAG | ACT | TCA | AAA | GCT | CCG | GTA | GAA | AAT | ACA |
| 6 | GCT | GAA | GTA | GAG | ACT | TCA | AAA | GCC | CCA | GTA | GAA | AAT | ACA |
| 7 | GCT | GAA | GTA | GAG | ACT | TCA | AAA | GCC | CTG | GTT | CAA | AAT | AGA$_{661}$ |

A wide variety of proteins are synthesized in precursor forms with subsequent processing to mature active proteins. For example, insulin, which in its active form is a two chain polypeptide, is synthesized as a single polypeptide chain (proinsulin) that is subsequently converted to mature insulin following proteolytic removal of an internal polypeptide. Also, the alkaline and neutral proteases of B. subtilis and B. amyloliquefaciens are synthesized as preproenzymes. It has not been previously known though that lysostaphin was synthesized as a preproenzyme. As shown in Table I, conversion of the alkaline and netural protease proenzymes to mature enzymes involves a similar cleavage site as does the conversion of prolysostaphin to lysostaphin.

TABLE I

Comparison of Preprolysostaphin With Bacillus Preproproteases

| Enzyme | Number of Residues Prepro Sequence | Number of Residues Mature | Final Cleavage Site |
|---|---|---|---|
| Subtilisin | | | |
| B. subtilis | 106 | 275 | HisGluTyr ↓ AlaGlnSerVal |
| B. amyloliquefaciens | 107 | 275 | HisAlaTyr ↓ AlaGlnSerVal |
| Neutral Protease | | | |
| B. subtilis | 221 | 300 | ValGluHis ↓ AlaAlaAlaThr |
| B. amyloliqufaciens | 221 | 300 | ValGluHis ↓ Ala AlaThrThr |
| Lysostaphin | 143 | 246 | AlaLeuArg ↓ AlaAlaThrHis |

The amino terminal sequence of purified mature lysostaphin from S. simulans determined by Edman degradation, Ala-Ala-Thr-His-Glu, corresponds to amino acids 144–148 of the preprolysostaphin sequence encoded by the 1.5 kbp DNA fragment of pRG5. The amino acid composition of mature lysostaphin predicated from the DNA sequence showed excellent correlation with the experimentally determined amino acid composition of purified lysostaphin obtained from S. simulans (NRRL B-2628) culture supernatants by Trayer et al., J. Biol. Chem., Vol. 245, pp. 4842–4846. Mature active lysostaphin, as determined from the predicated sequence, has a molecular weight of approximately 26,920 daltons. As shown in Formula IIA, conversion of the proenzyme to mature lysostaphin involves cleavage of the Arg-Ala bond at residues 143–144 of preprolysostaphin encoded by the 1.5 kbp DNA fragment.

EXAMPLE 3

Expression of Lysostaphin in E. coli JM105/pRG5 Transformants

A late logarithmic phase culture of E. coli JM105 transformed with pRG5, grown in 20 ml LB medium containing 50 μg/ml ampicillin, was harvested by centrifugation, and washed with Tris-saline buffer (TSB-10 mM Tris, 30 mM NaCl, pH 8.0). The pellet was resuspended in 1 ml of TSB and sonicated for 2 min at 0° C. The culture supernatant was concentrated 20 fold by ultrafiltration using an Amicon YM10 membrane. Lysostaphin activity was found in the supernatatant (65% of total), periplasmic (15%), and cytoplasmic (20%) fractions prepared as above.

Rabbit antibodies to lysostaphin purified from S. simulans supernatants were prepared and purified by affinity chromatography according to Recsei et al., J. Biol. Chem., Vol. 257, pp. 7196–7202 (1982) and utilized in immunoblotting experiments to localize and characterize lysostaphin and prolysostaphin produced by both E. coli JM105/pRG5 and S. simulans.

Purified goat antibodies to rabbit immunoglobulins were conjugated to alkaline phosphatase (Sigma) by standard techniques. For immunoblotting samples were subjected first to sodium dodecyl sulfate (SDS) polyacrylamide gel electrophoresis followed by transfer of separated proteins to nitrocellulose sheets using standard techniques. Immunoreactive proteins on the nitrocellulose filters were detected by incubating the filters first with rabbit antibody to lysostaphin and then with anti-rabbit immunoglobulin conjugated to alkaline phosphatase. The chromogenic substrate, 5-bromo-4-chloroindoxyl phosphate plus nitroblue tetrazolium, was used to detect alkaline phosphatase activity as described by Blake et al., Anal. Biochem, Vol. 136, pp. 175–179 (1984).

FIG. 1 depicts the results of the immunoblotting experiments. The following samples were applied to the designated lanes, electrophoresed, transferred to filters, and reacted with anti-lysostaphin antibody: supernatants from *S. simulans* cultures taken at late-logarithmic (lanes 1 and 6), early stationary (lane 2), mid-stationary (lane 3), and late-stationary (lane 4) phases; *E. coli*/pRG5 supernatant (lane 8) and cell extract (lane 7) from late-logarithmic phase cultures. Mead-Johnson lysostaphin was applied to lanes 5 and 9. The positions of molecular weight standards are also shown in FIG. 1.

The immunoblotting tests demonstrated the presence of mature lysostaphin (MW 26,920) in the concentrated culture supernatant of late logarithmic phase *E. coli* JM105/pRG5 transformants (FIG. 1, lane 8). A cross-reacting protein with identical electrophoretic mobility was found in supernatant of lysostaphin producing *S. simulans* cultures.

Immunologic analysis of electrophoresed cellular extracts of late logarithmic phase *E. coli* MJ105/pRG5 transformants indicated the presence of two proteins reactive with lysostaphin antibody. The mature lysostaphin was present in relatively small amounts. In addition, a larger amount of a cross-reactive protein with an apparent molecular weight of 64,000 daltons was also seen in the *E. coli* cellular fraction (FIG. 1, lane 7). A cross-reactive protein with electrophoretic mobility identical to this larger protein was also seen in supernatants of *S. simulans*, harvested primarily after growth to late log phase. The larger cross-reacting protein is, most likely, prolysostaphin, since in both *S. simulans* and *E. coli* JM105/pRG5, it preceeds lysostaphin in appearance and disappears as mature lysostaphin accumulates (FIG. 1, lanes 1-4 and 8). The apparent overestimation of the molecular weight of prolysostaphin most likely results from decreased binding of SDS due to the high content of glutamic acid residues in the tandem repeats of the prolysostaphin sequence.

Lysostaphin, therefore, is synthesized as a preproenzyme. The signal sequence of the preprolysostaphin is cleaved upon vectorial transport of the polypeptide chain through the membrane. The resulting prolysostaphin is subsequently processed extracellularly to mature lysostaphin. Conversion to the mature active enzyme is accomplished by cleavage of the $Arg_{143}$–$Ala_{144}$ peptide bond. The amino terminal portion of prolysostaphin apparently is removed in stages, i.e., the entire proenzyme sequence is not all removed at the same time. This processing reaction occurs in the supernatant of stationary phase cultures of *S. simulans*. Since mature enzyme is also produced by cultures of *E. coli* JM105/pRG5 transformants, the proenzyme processing is either autocatalytic or involves similar processing activities which are present in both *E. coli* JM105 and *S. simulans*. *E. coli* JM105/pRG5 transformants, however, have the advantage that processing appears to occur intracellularly rather than extracellularly as in *S. simulans*.

EXAMPLE 4

Construction of Plasmids Which in Transformant Bacillus spp. Express Lysostaphin

*Bacillus* expression systems for production of cloned gene products have significant advantages over similar systems using *E. coli* as the host organism. *Bacillus* species normally secrete proteins readily into the surrounding medium. Because of this advantage, recombinant plasmids containing the 1.5 kbp DNA sequence coding for lysostaphin were constructed from plasmids that replicate in various *Bacillus* species.

Plasmid pRG5 was used as the source of the DNA encoding lysostaphin. Plasmid pRG5 DNA, digested with Hind III and Eco RI according to the conditions specified by the manufacturer, was fractionated by preparative electrophoresis in 1% agarose. The 1.5 kbp DNA fragment which codes for lysostaphin was located by ethidium bromide staining and transferred by electrophoresis to a DEAE-nitrocellulose filter strip. The strip was washed with NET buffer (0.15M NaCl, 0.1 mM EDTA, 0.02 MTris, pH 8.0) and the bound DNA was eluted by incubation of the strip in NET buffer containing 1M NaCl for 1 hour at 65° C. Ethidium bromide was removed from the DNA by twice extracting the solution with an equal volume of n-butanol. DNA was precipitated by addition of two volumes of cold 95% ethanol to the aqueous phase, collected by centrifugation, washed with 80% ethanol and dissolved in TE buffer (Example 1).

a. Plasmid pJP1

Recombinant plasmid, pJP1, a preferred embodiment of this invention, was constructed by inserting the 1.5 kbp DNA fragment coding for lysostaphin into the *Bacillus* plasmid pBC16, which carries the gene for tetracycline resistance. Plasmid pBC16, obtained from the collection of Richard P. Novick, Public Health Research Institute, New York, N.Y., was isolated from soil bacilli and is highly homologous to and incompatible with pUB110, a *S. aureus* plasmid specifying kanamycin resistance. pBC16 DNA was isolated from *B. subtilis* by the alkaline-SDS procedure described by Birnboim, Meth. Enzymol, Vol. 100, pp. 243-255 (1983). Cells from a 250 ml overnight culture grown in VY medium (25 g Difco veal infusion; 5 g Difco yeast extract/1 $H_2O$) were harvested by centrifugation, washed in TE buffer and resuspended in 5 ml of TEG buffer (25 mM Tris, 10 mM EDTA, 50 mM glucose, pH 8.0). Lysozyme (1 mg/ml) was added and the suspension was incubated at room temperature for 20 minutes. After addition of 10 ml of 0.2% NaOH-1% SDS, the mixture was incubated at 0° C. for 45 minutes. Ten ml of 3M postassium acetate-1.8M formic acid were then added and the mixture was further incubated at 0° C. for 30 minutes. The lysate thus obtained was centrifuged at 15,000×g for 20 minutes. Two volumes of 95% ethanol were added to the supernatant and the resulting precipitate, obtained after 15 minutes at room temperature, was collected by centrifugation at 10,000×g for 10 minutes, washed with 80% ethanol and dissolved in 0.5 ml TE buffer. Approximately 200 µg of closed circular pBC16 DNA was obtained with this procedure.

The plasmid DNA was linearized by Eco RI cleavage. A mixture of linearized pBC16 DNA (approximately 1 µg) and the 1.5 kbp DNA fragment coding for lysostaphin (about 1 µg) was blunt ended using DNA polymerase (Klenow fragment). T4 DNA ligase was then used to ligate the plasmid and fragment DNA together, thereby reforming closed circular plasmid DNA molecules.

Competent *B. subtilis* strain BD 170 cells, obtained from David Dubnau of Public Health Research Institute, New York, N.Y., were transformed with the ligated DNA (approximately 1 µg DNA per 0.1 ml of cells) according to the method of Contente et al., Mol. Gen. Genet., Vol. 167, pp. 251-258 (1979). The cells were then incubated at 37° C. for 90 minutes to allow expression of the plasmid's tetracycline resistance gene and plated on TBAB agar containing a selective amount of tetracyline (5 μg/ml) and suspended heat-killed *S. aureus* cells to indicate lysostaphin production.

Heat-killed *S. aureus* cells for measuring lysostaphin activity were prepared by autoclaving (40 min.) a stationary phase culture grown in 500 ml CYGP broth. The dead cells were centrifuged and resuspended in 10 ml sterile water. Two ml of this dead cell preparation was added to 500 ml TBAB agar for preparation of the indicator plates.

Approximately 1% of the *B. subtilis* cells transformed with the ligated DNA produced lysostaphin as indicated by the lysis of staphylococcal cells surrounding the *B. subtilis* colonies. pJP1 was obtained by restreaking one of the *B. subtilis* transformants on lysostaphin indicator plates several times until a completely stable clone was obtained.

Lysostaphin activity was present primarily in the supernatant fraction of *B. subtilis* BD 170/pJP1 transformants grown to stationary phase in liquid medium. Immunoblot analysis showed that a lysostaphin precursor form was secreted which was subsequently converted to mature lysostaphin. In addition, immunoblotting also showed the pressure of lysostaphin degradation products in culture supernatants which were minimized when phenylmethylsulfonyl fluoride, a serine-protease inhibitor, was added to the culture. It is thus likely that a serine-protease is secreted into the medium or present on the surface of *B. subtilis* BD170 cells.

b. pDF8 and pRP1

Two other recombinant plasmids, pDF8 and pRP1, containing the lysostaphin gene were constructed for transformation of *Bacillus* species essentially as provided in Example 4*a* for the construction of pJP1.

pDF8 was obtained by inserting the 1.5 kbp DNA fragment coding for lysostaphin into the Eco RI restriction site of plasmid pBD64, a kanamycin, chloramphenicol resistance plasmid obtained from the collection of David Dubnau, Public Health Research Institute, New York, N.Y. pDF8 was obtained, as above, following transformation of *B. subtilis* BD 170 with recircularized plasmids and planting such transformants on lysostaphin indicator plates containing 5 μg/ml chloramphenicol. pDF8 was selected following repeated restreaking of positive clones.

Likewise, pRP1 was constructed by inserting the 1.5 kbp DNA fragment which code for lysostaphin into the HpaI site of pSPV1, a chloramphenicol resistance plasmid obtained from Steven Projan, Public Health Research Institute, New York, N.Y. All subsequent steps for isolation of pRP1 were identical to those for the construction of pJP1 and pDF8.

EXAMPLE 5

Lysostaphin Expression in B. sphaericus 00/pJP1 Transformants

A number of *Bacillus* strains were transformed with pJP1 to obtain a suitable host for large scale production of lysostaphin. Transformants which produced large lysis halos on lysostaphin indicator plates were isolated and further characterized. Of the *Bacillus* strains screened, *B. sphaericus* strain 00, an organism isolated and maintained in the culture collection of the Public Health Research Institute, New York, N.Y., provides maximal production of lysostaphin.

*B. sphaericus* 00/pJP1 transformants were obtained by treating protoplasts obtained by lysozyme treatment of intact cells with pJP1 DNA in the presence of polyethylene glycol according to the method of Chang et al., Molec. Gen. Genet., Vol. 168, pp. 11-115 (1979). Following treatment, the cells were grown on DM3 regeneration plates in the presence of tetracyline (5 μg/ml) prior to assay on lysostaphin indicator plates.

*B. sphaericus* 00/pJP1 transformants grown on VY or CYGP medium produced and secreted approximately 150 mg mature active lysostaphin per liter of culture medium. This amount is about five times the amount produced by *S. simulans* under the best fermentation techniques currently available. Active lysostaphin accumulates in the growth medium with little degradation, even after prolonged incubation of cultures, and accounts for approximately 80% of total extracellular protein. Lysostaphin isolated from *B. sphaericus* 00/pJP1 transformants is immunologically, electrophoretically and catalytically indistinguishable from that obtained from *S. simulans* cultures. Lysostaphin is isolaed from the growth medium in accordance with known fractional precipitation (salting out) procedures. Alternatively, a particularly effective purification is achieved by combining a precipitation and a chromatographic separation of the fermentation broth from cultures of lysostaphin-producing *B. sphaericus.* 00/pJP1 transformants.

Cells are removed from the fermentation broth, for example by centrifugation or ultrafiltration, and solid ammonium sulfate is added to the supernatant to 40-60%, preferably 50%, of saturation. After 1 hour at 4° C., the lysostaphin-containing precipitate is recovered by centrifugation. Recovery at this step is greater than 80%.

The precipitate is redissolved in a minimum volume of 10 mM sodium phosphate buffer (pH 7.00, 50 mM NaCl) and dialyzed against 100 volumes of the same buffer. After removal of any particulate material, the dialyzed solution is chromatographed on a cation exchange column (preferably Pharmacia FPLC Mono S) and eluted using a buffered gradient of increasing salt concentration from 0.05 to 0.25M NaCl. Recovery of lysostaphin for the single chromatographic step was more than 90%. Lysostaphin activity is associated with two major peaks. The later eluting peak of lysostaphin is comprised of non-covalent aggregates of the protein. These aggregates dissociate on dilution in buffer and under conditions of sodium dodecylsulfate polyacrylamide gel electrophoresis.

The lysostaphin that is purified from the culture medium of *B. sphaericus* 00/pJP1 transformants is substantially free of non-lysostaphin contaminants. Of special significance is that the *B. sphaericus* 00/pJP1 lysostaphin is substantially free of immunogenic staphylococcal contaminants.

I claim:

1. Recombinant plasmids containing a DNA sequence which codes for lysostaphin and which in transformant microbial hosts will express a gene encoding lysostaphin from *S. simulans* (NRRLB-2628).

2. Recombinant plasmids according to claim 1, in which the recombinant plasmid is selected from the group consisting of pRG5, pJP1, pDF8, and pRP1.

3. A recombinant plasmid according to claim 1 in which the recombinant plasmid is pRG5.

4. A recombinant plasmid according to claim 1 in which the recombinant plasmid is pJP1.

5. A recombinant plasmid according to claim 1 in which the recombinant plasmid is pDF8.

6. A recombinant plasmid according to claim 1 in which the recombinant plasmid is pRP1.

7. Transformant microorganism which produces lysostaphin, the microorganism being transformed by a recombinant plasmid containing a DNA sequence which codes for lysostaphin from *S. simulans* (NRRL B-2628).

8. Transformant microorganisms according to claim 7, in which the microorganisms are selected from the group consisting of *E. coli*, Yeast, *Streptomyces* spp., and *Bacillus* ssp.

9. Transformant microorganisms according to claim 7, in which the microorganisms are selected from the group consisting of *E. coli*, *B. subtilis* and *B. sphaericus*.

10. Transformant microorganism according to claim 7, in which the microorganism is *E. Coli* K-12 strain JM105.

11. Transformant microorganism according to claim 10, in which the recombinant plasmid is pRG5.

12. Transformant microorganism according to claim 7, in which the microorganism is *B. sphaericus* strain 00.

13. Transformant microorganism according to claim 12, in which the recombinant plasmid is pJP1.

14. Transformant microorganism according to claim 7, in which the microorganism is *B. subtilis* BD170.

15. Transformant microorganism according to claim 14, in which the recombinant plasmid is pJP1.

16. Transformant microorganism according to claim 14, in which the recombinant plasmid is pDF8.

17. Transformant microorganism according to claim 14, in which the recombinant plasmid is pRP1.

18. A method of expressing lysostaphin comprising transforming a microorganism by a recombinant plasmid which contains a DNA sequence which codes for lysostaphin from *S. simulans* (NRRL B2628) and culturing the transformed microorganism under conditions suitable for growth and expression of lysostaphin.

19. A DNA fragment selected from the group consisting of:
(a) a 1.5 kilobase DNA fragment coding for lysostaphin having the following amino acid sequence which comprises the following nucleotide sequence
1: ccggaactcttgaatgtttagttttgaaaattccaaaaaaaaacctactttcttaatatt
61: gattcatattattttaacacaatcagttagaatttcaaaaatctaaagtcaattttga
121: gtgtgtttgtatatttcatcaaaatcaatcaatattatttactttcttcatcgttaaaa
181: aatgtaatatttataaaaaatatgctattctcataaatgtaataataaattaggaggtatt
241: aaggttgaagaaaacaaaaaacaattattatacgagacctttagctattggactgagtac f-MetLysLysThrLysAsnAsnTyrTyrThrArgProLeuAlaIleGlyLeuSerThr
301: atttgccttagcatctattgtttatggagggattcaaaatgaaacacatgcttctgaaaa PheAlaLeuAlaSerIleValTyrGlyGlyIleGlnAsnGluThrHisAlaSerGluLys
361: aagtaatatggatgtttcaaaaaaagtagctgaagtagagacttcaaaagccccagtaga SerAsnMetAspValSerLysLysValAlaGluValGluThrSerLysAlaProValGlu
421: aaatacagctgaagtagagacttcaaaagctccgtagaaaatacagctgaagtagagac AsnThrAlaGluValGluThrSerLysAlaProValGluAsnThrAlaGluValGluThr
481: ttcaaaagctccagtagaaaatacagctgaagtagagacttcaaaagctccagtagaaaa SerLysAlaProValGluAsnThrAlaGluValGulThrSerLysAlaProValGlusAsn
541: tacagctgaagtagagacttcaaaagctccggtagaaaatacagctgaagtagagacttc ThrAlaGluValGluThrSerLysAlaProValGluAsnThrAlaGluValGluThrSer
601: aaaagccccagtagaaaatacagctgaagtagagacttcaaaagcccctggttcaaaatag LysAlaProValGluAsnThrAlaGluValGluThrSerLysAlaLeuValGlnAsnArg
661: aacagctttaagagctgcaacacatgaacattcagcacaatggttgaataattacaaaaa ThrAlaLeuArgAlaAlaThrHisGluHisSerAlaGlnTrpLeuAsnAsnTyrLysLys
721: aggatatggttacggtccttatccattaggtataaatggcggtatgcactacggagttga GlyTyrGlyTyrGlyProTyrProLeuGlyIleAsnGlyGlyMetHisTyrGlyValAsp
781: tttttttatgaatattggaacaccagtaaaagctatttcaagcggaaaaatagttgaagc PhePheMetAsnIleGlyThrProValLysAlaIleSerSerGlyLysIleValGluAla
841: tggttggagtaattacggaggaggtaatcaaataggtcttattgaaaatgatggagtgca GlyTrpSerAsnTyrGlyGlyGlyAsnGlnIleGlyLeuIleGluAsnAspGlyValHis
901: tagacaatggtatatgcatctaagtaaatataatgttaaagtaggagattatgtcaaagc ArgGlnTrpTyrMetHisLeuSerLysTyrAsnValLysValGlyAspTyrValLysAla
961: tggtcaaataatcggttggtctggaagcactggttattctacagcaccacatttacactt GlyGlnIleIleGlyTrpSerGlySerThrGlyTyrSerThrAlaProHisLeuHisPhe
1021: ccaaagaatggttaattcatttcaaattcaactgcccaagatccaatgcctttcttaaa GlnArgMetValAsnSerPheSerAsnSerThrAlaGlnAspProMetProPheLeuLys
1081: gagcgcaggatatggaaaagcaggtggtacagtaactccaacgccgaatacaggttgaa SerAlaGlyTyrGlyLysAlaGlyGlyThrValThrProThrProAsnThrGlyTrpLys
1141: aacaaacaaatatggcacactatataaatcagagtcagctagcttcacacctaatacaga ThrAsnLysTyrGlyThrLeuTyrLysSerGluSerAlaSerPheThrProAsnThrAsp
1201: tataataacaagaacgactggtccatttagaagcatgccgcagtcaggagtcttaaaagc IleIleThrArgThrThrGlyProPheArgSerMetProGlnSerSlyValLeuLysAla
1261: aggtcaaacaattcattatgatgaagtgatgaaacaagacggtcatgtttgggtaggtta GlyGlnThrIleHisTyrAspGluValMetLysGlnAspGlyHisValTrpValGlyTyr
1321: tacaggtaacagtggccaacgtatttacttgcctgtaagaacatggaataaatctactaa ThrGlyAsnSerGlyGlnArgIleTyrLeuProValArgThrTrpAsnLysSerThrAsn
1381: tactttaggtgttctttggggaactataaagtgagcgcgcttttttataaacttatatgat ThrLeuGlyValLeuTrpGlyThrIleLys
1441: aattagagcaaataaaaatttttctcattcctaaagttgaagc, (b) A DNA fragment coding for mature lysostaphin comprising nucleotides 674-1411 in (a),
(c) a DNA fragment coding for preprolysostaphin comprising nucleotides 245-1411 in (a),
(d) a DNA fragment coding for prolysostaphin comprising nucleotides 356-1411 in (a), and
(e) a DNA fragment coding for the lysostaphin signal peptide comprising nucleotides 245-355 in (a).

20. The DNA fragment of claim 19 coding for mature lysostaphin.

21. The DNA fragment of claim 19 coding for prepolysostaphin.

22. The DNA fragment of claim 19 coding for polysostaphin.

23. The DNA fragment of claim 19 coding for the lysostaphin signal peptide.

* * * * *

UNITED STATES PATENT AND TRADEMARK OFFICE
CERTIFICATE OF CORRECTION

PATENT NO. : 4,931,390
DATED : June 5, 1990
INVENTOR(S) : Paul A. Recsei

It is certified that error appears in the above-indentified patent and that said Letters Patent is hereby corrected as shown below:

Col. 4, line 52, "67077" should read --69764--.

Signed and Sealed this

Third Day of October, 1995

Attest:

BRUCE LEHMAN

*Attesting Officer*     *Commissioner of Patents and Trademarks*